United States Patent [19]

Nohda et al.

[11] 4,390,255

[45] Jun. 28, 1983

[54] EYE-REFRACTOMETER DEVICE

[75] Inventors: Masao Nohda, Yokohama; Izumi Umemura, Kawasaki; Toshiyuki Arai, Yokohama, all of Japan

[73] Assignee: Nippon Kogaku K.K., Tokyo, Japan

[21] Appl. No.: 375,677

[22] Filed: May 6, 1982

Related U.S. Application Data

[63] Continuation of Ser. No. 104,834, Dec. 18, 1979, abandoned.

[30] Foreign Application Priority Data

Dec. 22, 1978 [JP] Japan ................................ 53/158846

[51] Int. Cl.$^3$ .............................................. A61B 3/10
[52] U.S. Cl. .................................... 351/212; 351/237
[58] Field of Search ................. 351/6, 9, 11, 13, 16, 351/7

[56] References Cited

U.S. PATENT DOCUMENTS

| | | | |
|---|---|---|---|
| 3,136,839 | 6/1964 | Safir | 351/6 |
| 3,715,166 | 2/1973 | Leighty | 351/6 |
| 4,125,320 | 11/1978 | Rassow et al. | 351/13 |

Primary Examiner—John K. Corbin
Assistant Examiner—Rodney B. Bovernick

Attorney, Agent, or Firm—Fitzpatrick, Cella, Harper & Scinto

[57] ABSTRACT

An eye-refractometer device has a beam splitter, a projection optical system provided in one light path of the beam splitter for projecting a light beam into the pupil of an eye to be examined and scanning the light beam, a condenser optical system provided in the other light path of the beam splitter for receiving the reflected light from the retina of the eye, the condenser optical system comprising a condenser lens, a diaphragm member and a light-receiving member, and a signal processing system for processing the signal from the light-receiving member. Light beam rotating means for rotating the light beam about the optic axis is provided between the beam splitter and the eye. The light-receiving member is fixedly disposed at a position substantially conjugate with the cornea of the eye with respect to the condenser lens and a plurality of light-receiving elements are provided on the light-receiving surface of the light-receiving member off the optic axis. The diaphragm member is fixedly disposed between the beam splitter and the light-receiving member. Phase difference detecting means for detecting the phase differences between the output signals from the plurality of light-receiving elements is provided as the signal processing system.

5 Claims, 8 Drawing Figures

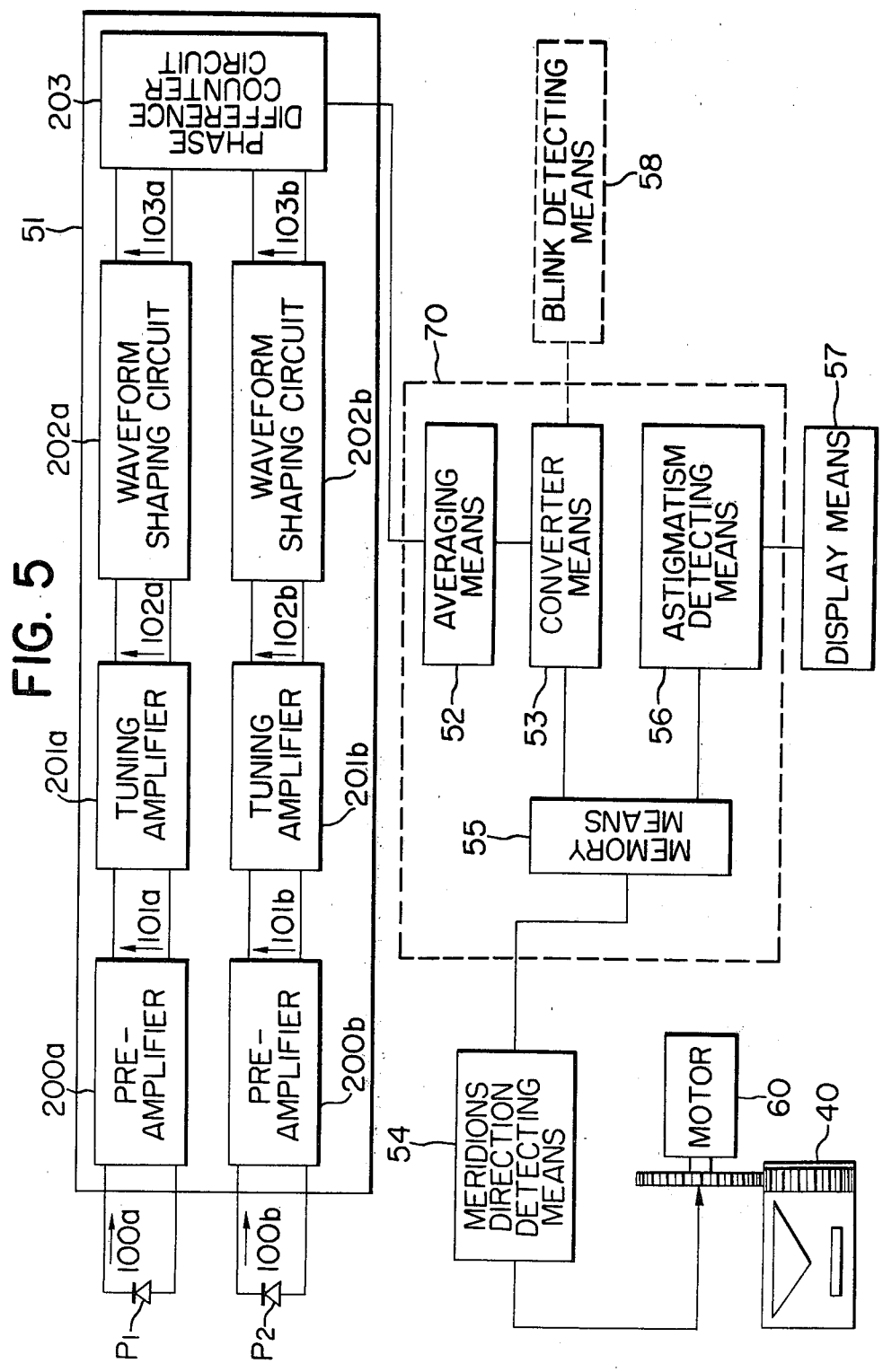

EYE-REFRACTOMETER DEVICE

This is a continuation of application Ser. No. 104,834, filed Dec. 18, 1979, now abandoned.

BACKGROUND OF THE INVENTION

1. Field of the Invention

This invention relates to an improvement over an eye refractometer device using retinoscopy.

2. Description of the Prior Art

Generally, in the measurement of the diopter of an eye, it is necessary to first detect the direction of the astigmatic principal meridians, and then measure the diopter in that direction. A device for carrying out such measurement by the use of retinoscopy is already known. Retinoscopy is such that a slit-like light is sent into the pupil of the eye to be examined and when that light is moved, the movement exhibited in the pupil by the reflected light from the retina of the eye is observed, whereby the neutralized condition in which the light becomes unmoved is found out. There are two types of such method, namely, one in which a lens having various refractive powers is disposed immediately before the eye to be examined so that the eye is observed from a predetermined position to obtain the diopter by a lens bringing about the neutralized condition, and one in which the eye is observed by varying the observation distance so that the diopter is obtained from a distance providing the neutralized condition. As the devices for photoelectrically measuring the diopter of the eye by retinoscopy, a device using the former method is disclosed in U.S. Pat. No. 3,136,839 and a device using the latter method is disclosed in U.S. Pat. No. 3,715,166. In these measuring devices, the entire device is rotated to detect the direction of the astigmatic axis of the eye to be examined and an accurate servo mechanism for making the entire device exactly coincident with the direction of the astigmatic principal meridians is indispensable. This has made the device complicated and bulky and has been prejudicial to quick measurement.

SUMMARY OF THE INVENTION

It is the object of the present invention to provide an eye-refractometer device which is simple and compact in construction and which can measure the diopter of eye accurately and quickly.

The present invention basically uses retinoscopy and consists in an eye-refractometer device which has a projection optical system provided in one light path of a beam splitter for projecting a light beam into a pupil of an eye to be examined and scanning the light beam, a condenser optical system provided in the other light path of the beam splitter for receiving the reflected light from the retina of the eye, said condenser optical system comprising a condenser lens, a diaphragm member and a light-receiving member, and a signal processing system for processing the signal from said light-receiving member, wherein light beam rotating means for rotating the light beam about the optic axis is provided between the beam splitter and the eye, the light-receiving member is fixedly disposed at a position substantially conjugate with the cornea of the eye with respect to the condenser lens and a plurality of light-receiving elements are provided on the light-receiving surface of the light-receiving member off the optic axis, the diaphragm member is fixedly disposed between the beam splitter and the light-receiving member, and phase difference detecting means for detecting the phase differences between the output signals from the plurality of light-receiving elements provided on the light-receiving member is provided as the signal processing system.

The invention will become more fully apparent from the following detailed description thereof taken in conjunction with the accompanying drawings.

BRIEF DESCRIPTION OF THE DRAWINGS

FIG. 5 is a block diagram of the electrical signal processing system according to an embodiment of the present invention.

DESCRIPTION OF THE PREFERRED EMBODIMENTS

Before the construction of the present invention is described, the principle of the invention will first be explained.

Figure 1:
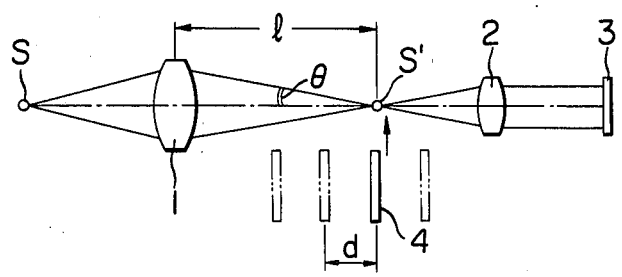
FIG. 1 shows the construction of an optical system illustrating the principle of the present invention.

Assume that, as shown in FIG. 1, the image S' of a point source of light S lying at a predetermined distance on the optic axis is formed by the first lens 1 at a distance l from that first lens 1 and that the light beam from the light source S is projected upon a light-receiving surface 3 by a second lens 2. Here, if a douser 4 lying at the distance l from the first lens 1 vertically crosses the optic axis from below to above on the plane of the paper of FIG. 1, the light-receiving surface 3 will become dark in a moment. If the douser 4 crosses the optic axis at a distance shorter than l a shadow will run on the light-receiving surface 3 from above to below. If the douser 4 crosses the optic axis at a distance nearer to the first lens 1, a shadow will also run on the light-receiving surface 3 from above to below, but the speed of the shadow will be slower. On the other hand, if the douser 4 crosses the optic axis at a distance more remote than the light source image S', a shadow will run on the light-receiving surface 3 from below to above in contrast with the foregoing and thus, the direction of movement of the shadow will be coincident with the direction of movement of the douser 4. If the douser 4 lies at a position still more remote from the first lens 1, the speed of movement of the shadow will become slower. Thus, depending on whether the douser 4 lies forwardly or rearwardly with respect to the light source image S', the movement of the shadow on the light-receiving surface 3 differs. Therefore, assuming that the douser 4 crosses the optic axis at a predetermined position and that the refractive power of the first lens 1 is varied, the position of the light source image S' is varied in accordance with the variation in refractive power of the first lens, whereby the movement of the shadow on the light-receiving surface 3 is varied. Specifically, if the refractive power of the first lens 1 is great to such an extent that the light source image S' is formed forwardly of the douser 4, the direction of movement of the shadow on the light-receiving surface 3 will be coincident with the direction of movement of the douser 4. Conversely, if the refractive power of the first lens 1 is small to such an extent that the light source image S' is formed rearwardly of the douser 4, the shadow on the light-receiving surface 3 will move in the direction opposite to the direction of movement of the douser 4. As the relative distance between the light source image S' formed by the first lens 1 and the douser 4 is greater, the speed of movement of the shadow becomes slower. Of course, if the light source image S' is formed at the position of the douser 4, the light receiving surface will become dark in a moment.

If the time required for the shadow on the light-receiving surface 3 to run from one end to the other end is t and the distance from the douser 4 to the light source image S' is d, the following relation is established and the foregoing description is summarized in this equation:

$$t = (2 \tan \theta)/v \cdot d$$

where $\theta$ represents the angle made by the conical light beam reaching the light source image S' with the optic axis, and v represents the speed at which the douser 4 vertically crosses the optic axis. It is seen from this equation that if the time t required for the shadow to run on the light-receiving surface is measured, d representing the position of the light source image can be obtained. The value of d corresponds to the refractive power of the first lens 1 and from this, the refractive power may immediately be obtained.

In the foregoing description, moving the douser across the optic axis is equivalent to taking out part of the light beam from the point light source in a slit form and causing that part to scan in the aperture of the first lens. If the first lens 1 is regarded as the eye to be examined, this is nothing other than so-called retinoscopy. The present invention is thus based on the principle of measuring the speed of movement of the shadow, instead of simply obtaining the neutralization point in retinoscopy, and obtaining the diopter of the eye to be examined from this.

Figure 2:
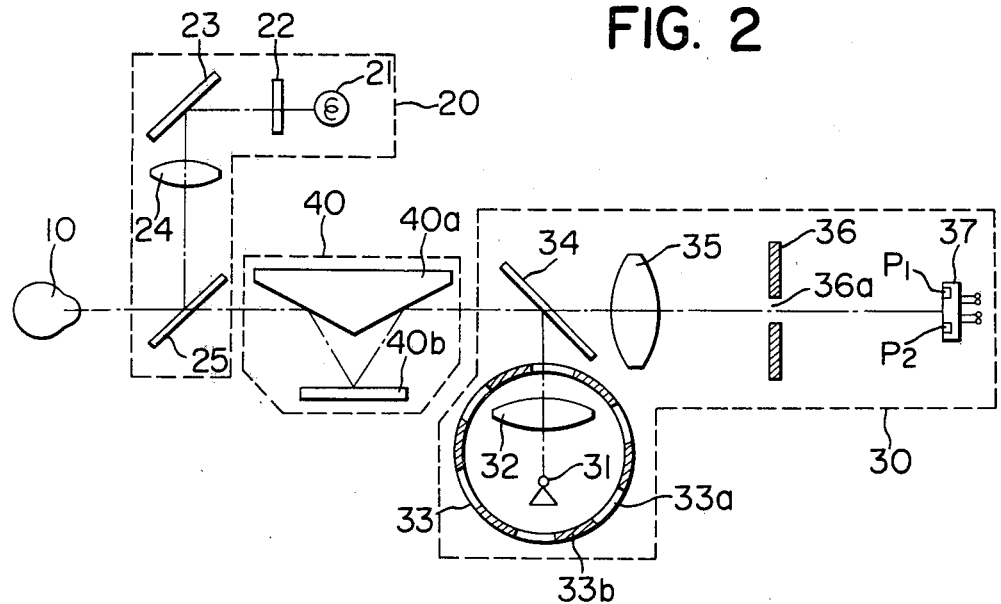
FIG. 2 shows the construction of the optical system according to an embodiment of the present invention.
Figure 3:
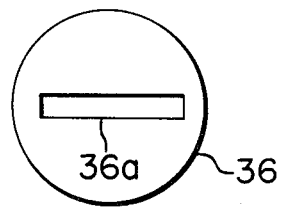
FIG. 3 shows the structure of the diaphragm member of FIG. 2.
Figure 4:
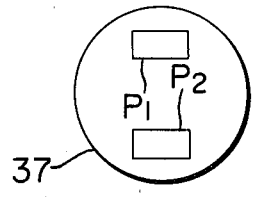
FIG. 4 shows the construction of the light-receiving member of FIG. 2.

The construction of the present invention will hereinafter be described with respect to an embodiment thereof. FIG. 2 is a cross-sectional view schematically showing the construction of the optical system according to an embodiment of the present invention. The present embodiment generally comprises a fixation optical system 20, testing, optical means 30 and light beam rotating means 40 provided between the fixation optical system 20 and the testing, optical means 30. In the fixation optical system 20, a light source 21 illuminates a target 22 and the light beam from the target 22 is reflected by a mirror 23 and substantially collimated by a collimater lens 24. This light beam is reflected by a partially reflecting mirror or beam splitter 25 and reaches the eye 10 to be examined which fixedly sees the target 22. The target 22 is movable in the direction of the optic axis and is placed each time at a position which can be fixedly seen by the eye to be examined in non-adjusted condition. The testing, optical means 30 includes a projection optical system for scanning a slit-like infrared light beam in the pupil of the eye 10 to be examined and a condenser optical system for condensing the reflected light from the retina of the eye 10 to be examined. The infrared light beam from an infrared light emitting diode 31 as the light source is made into a substantially parallel light beam by a projection lens 32 and reflected by a partially reflecting mirror or beam splitter 34, and projected into the pupil of the eye 10 through light beam rotating means 40 rotatively driven intermittently in a predetermined direction by a step motor (not shown). The shown light beam rotating means 40 is merely an example and comprises a triangular prism 40a and a mirror 40b. The light-emitting diode 31 and the projection lens 32 are disposed within a rotary cylinder 33 rotatable about an axis perpendicular to the optic axis of the projection lens 32, and the light beam reaching the beam splitter 34 is chopped by a slit-like opening 33a provided in the side of the rotary cylinder 33 and becomes a slit-like light beam having a rectilinear cross-section. Accordingly, with the rotation of the rotary cylinder 33, the slit-like light beam scans the interior of the pupil of the eye 10 to be examined. Of the light beam projected into the pupil of the eye 10 to be examined, the light reflected by the retina of the eye and again passing through the beam splitter 34 via the light beam rotating means 40 is condensed by a condenser lens 35. A diaphragm member 36 as shown in FIG. 3 having a slit-like opening 36a parallel to the lengthwise direction of the projected linear (slit-like) light beam is fixedly disposed rearwardly of the condenser lens 35, and a light-receiving member 37 is fixedly disposed further rearwardly of the diaphragm member 36. The position of the light-receiving member 37 is substantially conjugate with the cornea of the eye to be examined with respect to the condenser lens 35. Accordingly, the light passed through the slit-like opening 36a reaches the light-receiving member 37 and of that light, the reflected light from the cornea of the eye to be examined is condensed at the center of the light-receiving member 37. On the light-receiving surface of the light-receiving member 37, as shown in FIG. 4, two light-receiving elements $P_1$ and $P_2$ are disposed on a straight line orthogonal to the lengthwise direction of the slit-like opening 36a and equidistantly from the center of the light-receiving surface, and these two light-receiving elements $P_1$ and $P_2$ photocurrent signals proportional to the quantities of light received thereby.

In such a construction, the phase difference a between the signals from the two light-receiving elements $P_1$ and $P_2$ corresponds to the time t previously described in connection with the principle and required for the shadow to run on the light-receiving surface, and the diopter of the eye in the scanning direction of the slit-like light beam is obtained from this phase difference. If the light beam rotating means 40 is rotated, the scanning direction of the slit-like light beam is varied with the rotation, whereby measurement in the direction of various meridians of the eye to be examined is accomplished. While the slit-like light beam is rotated through 180° by the light beam rotating means 40, the phase difference between the signals from the two light-receiving elements $P_1$ and $P_2$ once assumes its maximum value and its minimum value respectively and these are repeated over 180° of a period. The scanning direction of the light beam, namely, the angular position of the light beam rotating means 40, when said phase difference assumes said maximum and minimum values is the direction of astigmatic principal meridians orthogonal to each other. If the eye to be examined has no astigmatism, the phase difference will not be varied even if the light beam rotating means 40 is rotated.

Here, the condenser lens 35 and the diaphragm member 36 are reverse in position but essentially similar in construction. However, in the construction shown in FIG. 2, the position of the diaphragm member 36 should desirably be coincident with the rear focus position of the condenser lens 35. If this is done, when the eye 10 to be examined is emmetropic, the retina of the eye and the position of the diaphragm member become conjugate with each other and the phase difference between the signals from the two light receiving elements $P_1$, $P_2$ becomes zero, thus enabling simplification of the signal processing system for obtaining the diopter from the phase difference signal.

Description will now be made of the signal processing system for obtaining the refractive power of the eye to be examined from the photocurrent signals produced by the two light-receiving elements.

Figure 6A:
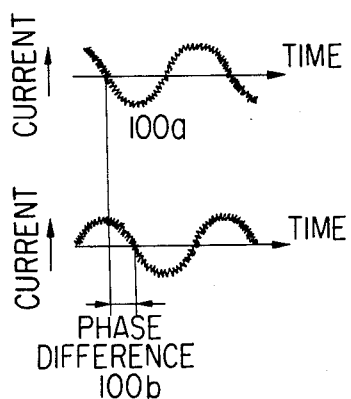
FIGS. 6A–6C shows the current signals in the electrical signal processing system of FIG. 5.
Figure 6B:
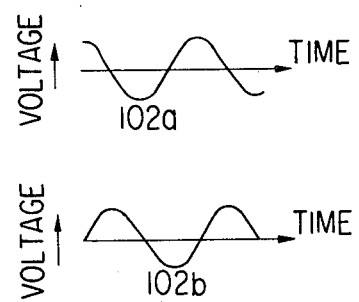
Figure 6C:
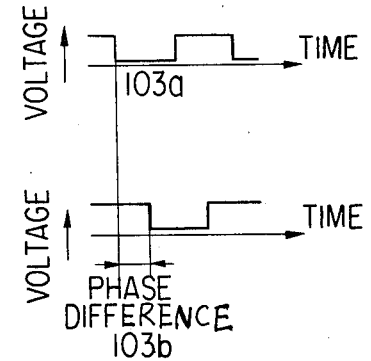

FIG. 5 is a block diagram of the signal processing system according to an embodiment of the present invention, and FIGS. 6A-6C schematically show signal waveforms processed by phase detecting means 51. The reflected lights from the retina of the eye which have impinged on the two light-receiving elements $P_1$ and $P_2$ produce photocurrents proportional to their respective quantities of light, and generally produce current signals 100a and 100b as shown in FIG. 6A. Since these photocurrents are minute signals, they are applied to pre-amplifiers 200a and 200b, respectively, from which they are generated as high level voltage signals 101a and 101b. These signals are applied to tuning amplifiers 201a and 201b so that their SN ratio may be improved, to thereby obtain output signals 102a and 102b (see FIG. 6B). The tuning frequencies of the tuning amplifiers are preadjusted to the chopping frequency of the light beam by the rotation of the rotary cylinder 33. These tuning amplifiers are designed so that the phase difference fluctuation between their inputs and outputs is very small so that the phase relation between the two input signals 101a and 101b is coincident with the phase relation between the two output signals 102a and 102b. The output signals 102a and 102b of the tuning amplifiers are applied to waveform shaping circuits 202 a and 202b. These circuits serve to shape the substantially sine wave input signals 102a and 102b into square wave signals 103a and 103b as shown in FIG. 6c so that the succeeding phase difference counter circuit 203 is operated. PLL (phase locked loop) circuits may be used as these waveform shaping circuits 202 in order to maintain constant the phase difference between the input and the output and to reduce the fluctuation thereof, whereby a good result may be obtained. The output signals 103a and 103b are applied to the phase difference counter circuit 203. The phase difference counter circuit 203 counts the phase difference between the two input signals 103a and 103b. The data counted by such phase difference counter circuit 203 is generated as the phase difference signal of phase difference detecting means 51.

The phase difference signal is then applied to averaging means 52. The averaging means 52 receives a plurality of phase difference signals and averages these. The number of the plurality of signals is the number of the slit-like light beams chopped and scanned by the rotation of the rotary cylinder 33 when the light beam rotating means 40 is intermittently rotated by the step motor 60. This number is appropriately selected in accordance with the number of revolutions of the rotary cylinder 33 and of the light beam rotating means 40 and the response characteristic of the light-receiving elements $P_1$ and $P_2$. The phase difference data averaged by the averaging means 52 is converted into diopter value by converter means 53. This conversion is obtained on the basis of a conversion table or a conversion formula and sufficient correction is made even if the relation between the phase difference signal and the diopter value is non-linear. A data by the averaging means 52 is provided as a diopter by the converter means 53 and this value is the diopter in the scanning direction of the slit-like light beam corresponding to the angular position of the light beam rotating means 40, namely, on the meridians in this direction. Meridians direction detecting means 54 detects the angular position of the light beam rotating means 40, namely, the scanning direction of the slit-like light beam, from the rotation of the light beam rotating means 40 or the step motor 60. Memory means 55 successively memorizes the diopter values from the converter means 53 by causing these diopter values to correspond to the angular position from the meridians direction detecting means 54. When the diopter have been memorized in the continuous range of 180°, astigmatism detecting means 56 detects from these diopter values the maximum value and the minimum value and the meridians directions corresponding to the respective values. These meridians directions are the direction of astigmatic principal meridians direction. When the diopter is constant, only this constant value is detected. These values are displayed in a predetermined display form by display means 57.

In such a signal processing system, the accuracy of measurement may be more improved and stabilized if blink detecting means 58 for detecting the disturbance of the data caused by the blinking of the eye to be examined is provided in side-by-side relationship with the converter means 53, for example, and if design is made such that when the disturbance of the data has been detected by the blink detecting means, the converter means 53 is stopped from operating and when it has been confirmed after a predetermined time interval that there is no longer disturbance of the data, the converter means is again operated. Of course, this blink detecting means can remove not only the noise resulting from the blinking of the eye to be examined but also the noise resulting from any other cause. Also, a third light-receiving element may be disposed around the rotary cylinder 33 to take out a constantly existing stray light component and mix this with the output signals of the light-receiving elements as an antiphase component, whereby noise component can be considerably removed.

If the processing from the averaging means 52 to the astigmatism detecting means 56 in the above-described signal processing system is carried out by a so-called computer 70, it is possible to effect very high speed and accurate processing. Further, if all the processing up to the conversion of the values displayed by the display means 57 and the output of the data is governed and controlled by the computer, there may be provided a completely automatic measuring device. It is also possible to design the device such that the diopter value for each by the aforementioned converter means is intactly recorded in succession and from these data, the examiner detects the maximum diopter, the minimum diopter and the astigmatic axis. Also, in the above-described embodiment, the light beam rotating means 40 is intermittently rotated by the step motor 60, whereas this is not restrictive but the light beam rotating means may be continuously rotated at a uniform speed. In this case, the phase difference outputs from the phase difference detecting means 51 strictly correspond to different meridians directions, but phase difference information for all the diametral line directions can be likewise obtained by regarding the average value by the averaging means 52 as the phase difference in the meridians direction corresponding to the center angle in the range over which the light beam rotating means 40 is slightly rotatively displaced during the while that a plurality of phase difference signals are produced by the phase difference detecting means 51, namely, during the while that the rotary cylinder 33 chops a plurality of light beams.

In the above-described construction of the present invention, moving members are only the rotary cylinder and the light beam rotating means and no servo mechanism is required and thus, the construction has become very simple and the configuration of the entire device has become very compact. Moreover, these rotating members need not be reciprocally moved but only must be rotated in a predetermined direction and this is advantageous for high speed of the measurement and as long as the response speeds of the light-receiving elements permit, the chopping of the slit-like light beam by the rotary cylinder is quickened to thereby enable a great deal of data to be taken out within a predetermined time. Also, by making the most of the advantage that a great deal of data can be obtained within a short time, a plurality of measurement data in a certain meridians direction are taken out and averaged, thus further enhancing the accuracy of measurement in spite of unstable factors such as fine movement from fixation of the eye to be examined.

On the other hand, in the conventional measuring device of such type, the factor of noise component has resided in that stray light is created chiefly by the movement of the optical member forming the measuring optical system, whereas in the construction of the present invention, only the rotary cylinder 33 and the light beam rotating means 40 are steadily rotated for the measurement and these effect no irregular movement, so that there is no danger of creating stray light to produce a great noise component. Also, the optical system is always fixed and therefore, the reflected light from the cornea of the eye to be examined which provides the greatest impediment in the measurement lies always at a predetermined position between the two light-receiving elements, thus enabling the flare from the cornea to be sufficiently removed.

As has hitherto been described, the present invention can not only achieve its intended purpose but also has various advantages and thus, provides an excellent eye-refractometer device.

We claim:

1. An eye-refractometer device for measuring the refractive power of an eye to be examined comprising:
   a first beam splitter;
   a second beam splitter disposed on that side of said first beam splitter which is adjacent to the eye;
   a projection optical system provided in one light path of said first beam splitter for projecting a slit-like light beam into the pupil of an eye to be examined by way of said first beam splitter and scanning said slit-like light beam in a direction perpendicular to the lengthwise direction of said slit-like beam;
   a condenser optical system provided in the other light path of said first beam splitter for receiving the reflected light from the retina of said eye by way of said first beam splitter, said condenser optical system including a fixed condenser lens, a diaphragm member fixedly disposed substantially at a focus position of said condenser lens, and a light-receiving member fixedly disposed rearwardly of said diaphragm member, said diaphragm member having a slit-like opening parallel to the lengthwise direction of said projected slit-like beam, and said light receiving member having two light-receiving elements fixedly disposed off the optic axis of said condenser lens and symmetrical with respect to the optic axis in a direction coincident with the scanning direction of said slit-like beam;
   a signal processing system for processing the signal from said light-receiving member and having phase difference detecting means for detecting the phase difference between the output signals from said two light-receiving elements and having averaging means for generating the average value signal of the plurality of signals from said phase difference detecting means;
   a target optical system for directing the target light to the eye by way of said second beam splitter; and
   light beam rotating means disposed between said first beam splitter and said second beam splitter for rotating said light beam about the center of the light path, whereby the scanning direction of the slit-like light beam supplied by said projection optical system is rotated at the eye by means of said light beam rotating means, while the scanning direction of the slit-like beam which is reflected by the fundus of the eye, passes again through said light beam rotating means and reaches said condenser optical system, is kept constant without being subject to the rotation by said light beam rotating means, and whereby all members constituting said condenser optical system are kept fixed and no servo system is needed, thus precise and quick refractive power of the eye being measured.

2. An eye-refractometer device according to claim 1, wherein said light beam rotating means includes a triangular prism and a mirror.

3. An eye-refractometer device according to claim 2, wherein said projection optical system includes an infrared light emitting diode.

4. An eye-refractometer device for measuring the refractive power of an eye to be examined comprising:
   a first beam splitter;
   a second beam splitter disposed on that side of said first beam splitter which is adjacent to the eye;
   a projection optical system provided in one light path of said first beam splitter for projecting a slit-like light beam into the pupil of an eye to be examined by way of said first beam splitter and scanning said slit-like light beam in a direction perpendicular to the lengthwise direction of said slit-like beam;
   a condenser optical system provided in the other light path of said first beam splitter for receiving the reflected light from the retina of said eye by way of said first beam splitter, said condenser optical system including a fixed condenser lens, and a fixed diaphragm member and a light-receiving member fixedly disposed rearwardly of said condenser lens, said diaphragm member having a slit-like opening parallel to the lengthwise direction of said projected slit-like beam, and said light receiving member having two light-receiving elements fixedly disposed off the optic axis of said condenser lens and symmetrical with respect to the optic axis in a direction coincident with the scanning direction of said slit-like beam;

a signal processing system for processing the signal from said light-receiving member and having phase difference detecting means for detecting the phase difference between the output signal from said two light-receiving elements and having averaging means for generating the average value signal of the plurality of signals from said phase difference detecting means;

a target optical system for directing the target light to the eye by way of said second beam splitter;

means for rotating scanning directions of the slit-like light beam at the eye about the center of the light path; and means for maintaining constant the scanning direction of the slit-like light beam at said light receiving member.

5. An eye-refractometer device according to claim 4, wherein said rotating means and said maintaining means commonly have a triangular prism and a mirror disposed between said first and second beam splitters.

* * * * *